United States Patent [19]

El-Menshawy et al.

[11] Patent Number: 4,482,537

[45] Date of Patent: Nov. 13, 1984

[54] SKIN CONDITIONING COMPOSITION

[75] Inventors: El-Sayed El-Menshawy, Holmdel; Richard Dixon, Aberdeen, both of N.J.

[73] Assignee: Charles of the Ritz Group Ltd., New York, N.Y.

[21] Appl. No.: 533,714

[22] Filed: Sep. 19, 1983

[51] Int. Cl.³ .......................... A61K 7/15; A61K 7/42; A61K 7/44; A61K 31/16
[52] U.S. Cl. ......................................... 424/59; 424/60; 424/73; 424/78; 424/80; 424/81; 424/273 R; 424/274; 424/320; 424/358; 424/359; 424/361; 424/362; 424/363; 424/365
[58] Field of Search .................... 424/59, 60, 358, 359, 424/365, 73, 361, 273, 274, 320

[56] References Cited

U.S. PATENT DOCUMENTS 4,146,649  3/1979  Siegel et al. .......................... 424/361

FOREIGN PATENT DOCUMENTS 673730  11/1963  Canada ................................ 424/361
5025741  3/1975  Japan .................................. 424/359

OTHER PUBLICATIONS

Scafidi et al., Cosmetics & Toiletries, vol. 95, 4/1980, pp. 65, 66, 69, 70, 71 and 72.
Brooks, Cosmetics & Toiletries, vol. 95, 3/1980, pp. 73, 74, 76.
Kass, Cosmetics & Toiletries, vol. 95, 4/1980, pp. 101, 106 to 108, 110 to 112, 114, 121, 124, 126 & 127.
Hermsdorf, Cosmetics & Toiletries, vol. 95, 4/1980, pp. 61 to 63.
Seldner, Cosmetics & Toiletries, vol. 95, 3/1980, pp. 85 & 86.
Technical Data Sheet on Glucam (Amerchol Corporation).
Technical Data Sheet on Edenol 302 (Henkel Corporation).

*Primary Examiner*—Dale R. Ore
*Attorney, Agent, or Firm*—Lawrence S. Levinson; Burton Rodney

[57] ABSTRACT

A skin conditioning composition is provided which may take the form of an after-bath splash and which includes a unique combination of ingredients which imparts staying power to the skin conditioning ingredients, which unique combination includes an alkoxylated methyl glucose derivative, such as a propoxylated methyl glucoside, and a propylene glycol dicaprylate/dicaprate.

11 Claims, No Drawings

SKIN CONDITIONING COMPOSITION

FIELD OF THE INVENTION

The present invention relates to skin conditioning compositions and especially moisture replenishing compositions which include a combination of an alkoxylated methyl glucose derivative and a propylene glycol dicaprylate/dicaprate.

BACKGROUND OF THE INVENTION

Until now, most skin moisturizer compositions have been formulated as creams and lotions which include an oil as a major ingredient. Such creams and lotions which include moisturizer ingredients have been found to adhere or stay on the skin for far greater periods than clear solutions such as after-bath splashes, skin toners and the like. However, the creams and lotions do impart a greasy sticky feel to the skin and may be messy and stain clothing. Accordingly, a non-cream non-lotion non-greasy moisturizer composition in the form of a clear solution which is effective in treating dry skin and which remain on the skin for extended periods of time would indeed fulfill a long-felt want.

DESCRIPTION OF THE INVENTION

In accordance with the present invention, an improved non-greasy skin conditioning and moisturizing composition is provided which is clear and non-greasy to the skin and touch and which forms a long-lasting film which stays on the skin for extended periods. The composition of the invention which will usually be in the form of a clear solution, includes one or more skin-conditioning agents and/or skin feel enhancers and/or humectants, one or more alkoxylated methyl glucose derivatives and propylene glycol dicaprylate/dicaprate, optionally one or more preservatives, and water as a carrier. The composition of the invention will also optionally but preferably include one or more astringents and/or colorants and/or fragrances.

As indicated, the composition of the invention includes a unique combination of ingredients that aids in forming a long-lasting skin-conditioning film, which combination includes (A) one or more alkoxylated methyl glucose derivatives and (B) a propylene glycol dicaprylate/dicaprate which will be present in a weight ratio of (A) to (B) of within the range of from about 100:1 to about 1:1 and preferably from about 5:1 to about 1:1, and optimally from about 2:1 to about 1:1.

The alkoxylated methyl glucose derivative will be present in the composition of the invention in an amount of within the range of from about 0.1 to about 25%, and preferably from about 0.5 to about 4% by weight of the total composition. The alkoxylated methyl glucose derivative will preferably comprise a propoxylated methyl glucoside such as Glucam ® P-10, trademark of Amerchol Corporation (a unit of CPC Internation, Inc.). Glucam P-10 is also referred to by its CTFA adopted name of PPG-10 methyl glucose ether. PPG refers to polypropylene glycol. Examples of other alkoxylated methyl glucose derivatives that may be used herein include PPG-20 methyl glucose ether or polyethylene glycol (10 or 20) ether of methyl glucose.

The propylene glycol dicaprylate/dicaprate will be present in the composition of the invention in an amount within the range of from about 0.05 to about 10%, and preferably from about 1 to about 2.5% by weight of the total composition. The preferred propylene glycol dicaprylate/dicaprate used herein is referred to as Edenol 302, as designated by Henkel Corporation, Chemical Specialties Division.

The composition of the invention will also preferably include a hydrolyzed animal protein to enhance skin feel and promote formation of a water-soluble film, in an amount of within the range of from about 0.01 to about 5% and preferably from about 0.15 to about 1.5% by weight of the composition. The hydrolyzed animal protein will preferably be myristoyl hydrolyzed animal protein such as Lexein A-210, trademark of Inolex Chemicals, which normally is supplied in an ethanol solution.

The composition of the invention may optionally include from 0 to about 1.5% and preferably from about 0.1 to about 1% by weight of a preservative, such as imidazolidinyl urea (for example, Germall 115), methyl or propyl paraben, dimethyldimethoyl hydantoin, Dowicil 200 (Quaternium 15), that is, N-(3-chloroallyl)-hexaminium chloride, benzyl alcohol and/or phenoxyethanol, with imidazolidinyl urea and methyl paraben being preferred.

Water will be employed in the composition of the invention as a solvent and carrier and will be present in an amount within the range of from about 10 to about 50% and preferably from about 15 to about 35% by weight.

A polyol to enhance skin feel may be present in an amount within the range of from about 0.1 to about 10% and preferably from about 0.2 to about 4% by weight. Examples of such polyols (which will also serve as humectants) suitable for use herein include, but are not limited to, polyethylene glycol (for example, PEG 8), sorbitol, glycerin, polyoxyethylene (26) glyceryl ether (Liponic EG1), propylene glycol, 1,3-butylene glycol or hexylene glycol with polyoxyethylene (26) glyceryl ether being preferred.

The composition of the invention may optionally include a thickener in an amount within the range of from about 0 to about 1% and preferably from about 0.05 to about 0.7% by weight. A preferred thickener suitable for use herein is Carbopol 940 or Carbomer 940 which is hydrophilic acrylic polymer cross-linked with a polyfunctional agent and employed with an organic or inorganic base, preferably triethanolamine. Other examples of thickeners which may be employed herein include, but are not limited to, hydroxyethyl cellulose, hydroxy propylcellulose or xanthan gum.

Other skin conditioning agents which may optionally be present in the composition of the invention include allantoin, d- or dl-panthenol, sodium-2-pyrrolidone carboxylic acid, and the like. Such conditioning agents may be present in an amount within the range of from about 0.01 to about 5% and preferably from about 0.05 to about 2% by weight.

The astringents which may be included will be present in an amount within the range of from about 20 to about 90% and preferably from about 40 to about 80% by weight of the composition of the invention. Examples of such astringents suitable for use herein include ethanol and isopropyl alcohol.

The composition of the invention may be employed in formulating clear skin toners, after-bath splashes, after-shave lotions, colognes, pre-electric shave lotions, after-sun products and the like. Accordingly, such skin preparations may include, in addition to the ingredients set out above, certified water-soluble colorants as deemed necessary, fragrances in amounts within the range of from about 0 to about 35% and preferably from about 0.1 to about 20% by weight depending upon the ultimate use of the skin preparation, solubilizing agents, such as polyoxyethylene (13) octylphenyl ether, polyoxyethylene (20) sorbitan monolaurate, polyoxyethylene (20) oleyl ether, and the like.

The composition of the invention may also optionally include from 0 to about 10% by weight of one or more sun screen agents such as octyl dimethyl p-aminobenzoic acid or benzophenone 3 (Uvinul D-50).

Preferred formulations within the scope of the present invention contain from about 0.5 to about 4% by weight propoxylated methyl glucoside, from about 1 to about 2.5% by weight propylene glycol dicaprylate/-dicaprate, from about 0.15 to about 1.5% by weight hydrolyzed animal protein, from about 0.1 to about 1% by weight preservatives, from about 15 to about 35% by weight water, from about 40 to about 80% by weight ethanol and/or isopropyl alcohol, optionally from about 0.05 to about 0.5% sodium 2-pyrrolidone carboxylic acid, optionally from about 0.5 to about 2% by weight allantoin and/or panthenol.

The composition of the invention when applied to the skin has surprisingly high substantivity, that is, it remains on the skin for extended periods of time providing the desired and needed skin conditioning and moisturizing.

The skin preparations of the invention containing the unique film forming combination as set out above can be prepared by simply mixing all of the ingredients together, until a uniform mixture is obtained, preferably without heat, then aging, chilling, filtering and bottling.

The following Example represents a preferred embodiment of the invention. All temperatures are expressed in degrees Centigrade.

EXAMPLE

A skin conditioning composition in the form of a clear after-bath splash in accordance with the present invention having the following composition was prepared as described below.

| Ingredient | Parts by Weight |
| --- | --- |
| Ethanol (SDA 40 Regular) | 69 |
| Benzophenone 3 (UV absorber - Uvinul D-50) | 0.1 |
| Perfume oil | 2 |
| Sodium 2-pyrrolidone carboxylic acid (humectant) | 0.2 |
| Propoxylated methyl glucoside (film former) | 4 |
| Propylene glycol dicaprylate/dicaprate (film former) | 2 |
| Polyoxyethylene (26) glyceryl ether (feel enhancer) (Liponic EG1) | 2 |
| Myristoyl hydrolyzed animal protein (skin feel and film former) (Lexein A-210) | 1 |
| Deionized water | 20 |

The ultraviolet light absorber (Uvinul D-50) was added to the ethanol with mixing for 15 minutes. Thereafter each ingredient was separately added with mixing until a uniform mix was obtained. The final mix was then aged for 24 hours at ambient conditions, then chilled at 0°-4° C. and filtered through a No. 9 Ertel filter pad. The resulting skin conditioning product was in the form of a clear solution which when applied to the skin formed a thin film which remained on the skin for extended perods.

What is claimed is:

1. A non-greasy, non-cream, non-lotion skin conditioning and moisturizing composition in the form of a clear solution which upon application to skin forms a long-lasting skin-conditioning film, consisting essentially of hydrolyzed animal protein in an amount within the range of from about 0.01 to about 5% by weight, or a polyol selected from the group consisting of polyethylene glycol, sorbitol, glycerin, polyoxyethylene (26) glyceryl ether, propylene glycol, 1,3-butylene glycol, and hexylene glycol, said polyol being present in an amount within the range of from about 0.1 to about 10% by weight of said hydrolyzed animal protein and said polyol, water in an amount within the range of from about 10 to about 35% by weight, an astringent selected from the group consisting of ethanol, isopropyl alcohol and mixtures thereof in an amount within the range of from about 40 to about 90% by weight, a conditioning agent selected from the group consisting of allantoin, d-panthenol dl-panthenol and sodium 2-pyrrolidone carboxylic acid in an amount within the range of from about 0.01 to about 5% by weight; a preservative selected from the group consisting of imidazolidinyl urea, methyl paraben, propyl paraben, dimethyldimethoyl hydantoin, N-(3-chloroalkyl) hexaminium chloride, benzyl alcohol, phenoxyethanol and mixtures thereof in an amount within the range of from about 0 to about 1.5% by weight; from about 0 to about 1% by weight of a thickener selected from the group consisting of a cross-linked hydrophilic acrylic polymer, hydroxyethyl cellulose, hydroxypropyl cellulose and xanthan gum; one or more alkoxylated methyl glucose derivatives selected from the group consisting of polypropylene glycol methyl glucose ether and polyethylene glycol methyl glucose ether, in an amount within the range of from about 0.1 to about 4% by weight, and propylene glycol dicaprylate/dicaprate in an amount within the range of from about 0.05 to about 2.5% by weight, the alkoxylated methyl glucose derivative being present in a weight ratio to the propylene glycol dicaprylate/dicaprate of within the range of from about 5:1 to about 1:1, all of the above % by weight being based on the weight of the total composition.

2. The skin conditioning composition as defined in claim 1 in the form of a hydroalcoholic solution.

3. The skin conditioning composition as defined in claim 1 wherein said alkoxylated methyl glucose derivative is a propoxylated methyl glucoside.

4. The skin conditioning composition as defined in claim 1 in the form of an after-bath splash, skin toner, cologne, pre-electric shave lotion or after-shave lotion.

5. The skin conditioning composition as defined in claim 1 including a hydrolyzed animal protein to enhance formation of a water in soluble film.

6. The skin conditioning composition as defined in claim 5 wherein said hydrolyzed animal protein is myristoyl hydrolyzed animal protein.

7. The skin conditioning composition as defined in claim 1 including ethanol and water.

8. The skin conditioning composition as defined in claim 1 including sodium 2-pyrrolidone carboxylic acid as a conditioning agent.

9. The skin conditioning composition as defined in claim 1 including polyoxyethylene (26) glyceryl ether as a humectant.

10. The skin conditioning composition as defined in claim 1 including an ultraviolet light absorber.

11. The skin conditioning composition as defined in claim 1 including a fragrance.

* * * * *

UNITED STATES PATENT AND TRADEMARK OFFICE
CERTIFICATE OF CORRECTION

PATENT NO. : 4,482,537
DATED : November 13, 1984
INVENTOR(S) : El-Sayed El-Menshawy, et al.

It is certified that error appears in the above—identified patent and that said Letters Patent is hereby corrected as shown below:

Column 1, line 57, "Internation" should read
  --International--.
Column 4, line 13, "of" should read --or--.
Column 4, line 52, "in soluble" should read
  --insoluble--.

Signed and Sealed this

Fourteenth Day of May 1985

[SEAL]

Attest:

DONALD J. QUIGG

Attesting Officer      Acting Commissioner of Patents and Trademarks